US00PP34105P2

(12) United States Plant Patent
Ruigrok

(10) Patent No.: US PP34,105 P2
(45) Date of Patent: Apr. 5, 2022

(54) ***DAHLIA* PLANT NAMED 'BKDAGIGP'**

(50) Latin Name: *Dahlia hybrida*
Varietal Denomination: BKDAGIGP

(71) Applicant: BEEKENKAMP PLANTS B.V., Maasdijk (NL)

(72) Inventor: Sanne Helena Ruigrok, Hillegom (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/346,275

(22) Filed: Jun. 13, 2021

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — C. Anne Whealy

(57) ABSTRACT

A new and distinct cultivar of *Dahlia* plant named 'BKDAGIGP', characterized by its relatively tall, upright to somewhat outwardly spreading and sturdy plant habit; vigorous growth habit; freely basal branching habit; dense and bushy growth habit; dark green-colored leaves; freely flowering habit; large semi-double type inflorescences with purplish pink and white bi-colored ray florets; and good garden performance.

2 Drawing Sheets

Figure 1:
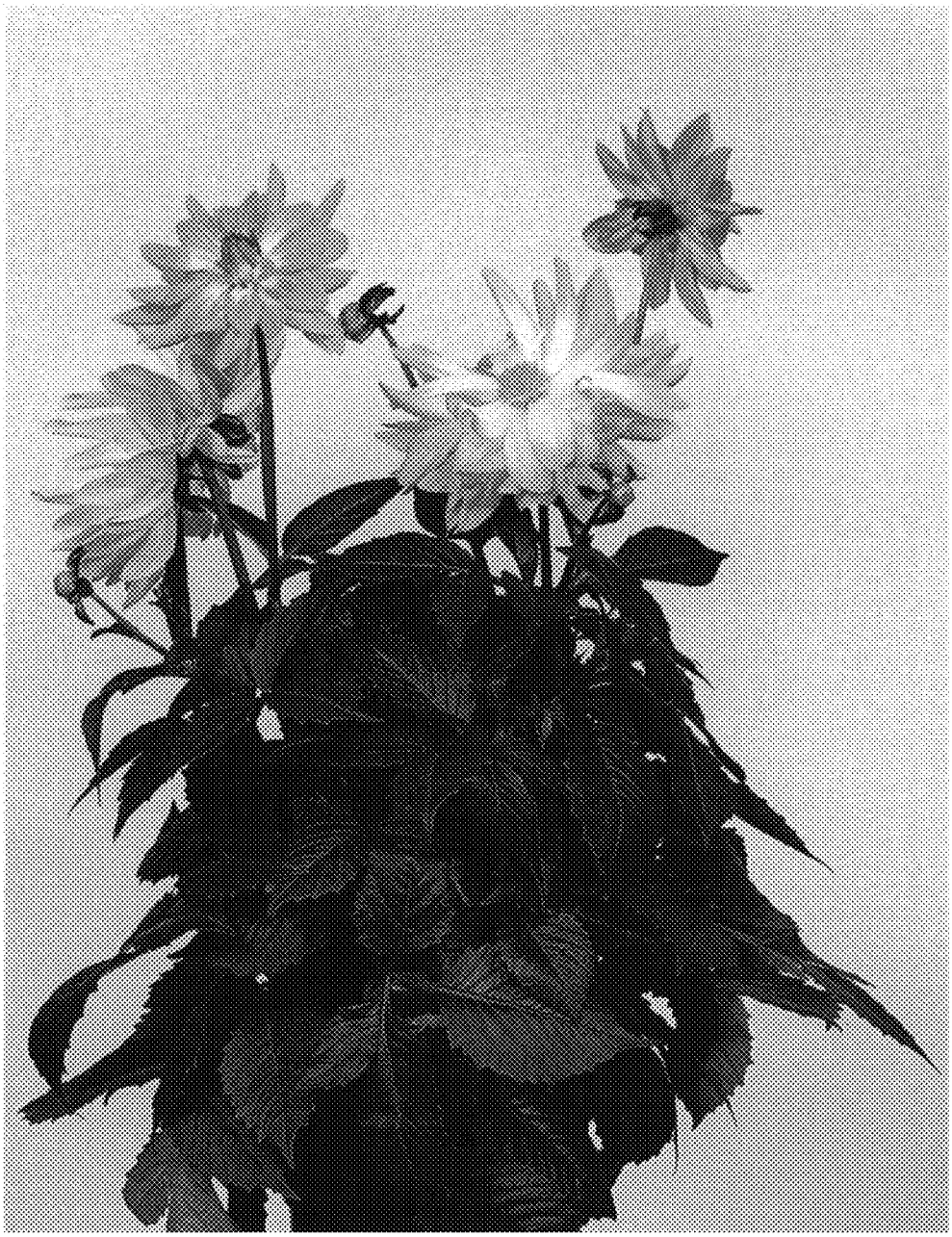

Botanical designation: *Dahlia hybrida.*
Cultivar denomination: 'BKDAGIGP'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Beekenkamp Plants B.V. of Maasdijk, The Netherlands on Oct. 20, 2020, application number 2020/2574. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Dahlia* plant, botanically known as *Dahlia hybrida* and hereinafter referred to by the name 'BKDAGIGP'.

The new *Dahlia* plant is a product of a planned breeding program conducted by the Inventor in Hillegom, The Netherlands. The objective of the breeding program is to create new vigorous container *Dahlia* plants with large inflorescences with attractive ray floret coloration.

The new *Dahlia* plant originated from a cross-pollination in September, 2016 in Hillegom, The Netherlands of *Dahlia hybrida* 'BKDAMAGRB', disclosed in U.S. Plant Pat. No.

30,691, as the female, or seed, parent with a proprietary selection of *Dahlia hybrida* identified as code number FET.S15.001.021, not patented, as the male, or pollen, parent. The new *Dahlia* plant was discovered and selected by the Inventor as a single flowering plant from within the progeny of the stated cross-pollination in a controlled greenhouse environment in Hillegom, The Netherlands in September, 2017.

Asexual reproduction of the new *Dahlia* plant by terminal cuttings in a controlled greenhouse environment in Hillegom, The Netherlands since March, 2018 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAGIGP'. These characteristics in combination distinguish 'BKDAGIGP' as a new and distinct *Dahlia* plant:

1. Relatively tall, upright to somewhat outwardly spreading and sturdy plant habit.
2. Vigorous growth habit.
3. Freely basal branching habit; dense and bushy growth habit.
4. Dark green-colored leaves.
5. Freely flowering habit.
6. Large semi-double type inflorescences with purplish pink and white bi-colored ray florets.
7. Good garden performance.

Plants of the new *Dahlia* differ primarily from plants of the female parent, 'BKDAMAGRB', in inflorescence size as plants of the new *Dahlia* have smaller inflorescences than plants of 'BKDAMAGRB'.

Plants of the new *Dahlia* differ primarily from plants of the male parent selection in plant size as plants of the new *Dahlia* are taller than plants of the male parent selection.

Plants of the new *Dahlia* can be compared to plants of *Dahlia hybrida* 'XXL Veracruz', not patented. In side-by-side comparisons, plants of the new *Dahlia* differ from plants of 'XXL Veracruz' in the following characteristics:

1. Plants of the new *Dahlia* are much taller than plants of 'XXL Veracruz'.
2. Ray floret color of plants of the new *Dahlia* are purplish pink and white bi-colored whereas ray florets of plants of 'XXL Veracruz' are violet and light pink bi-colored.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1) is a side perspective view of a typical flowering plant of 'BKDAGIGP' grown in a container.

Figure 2:
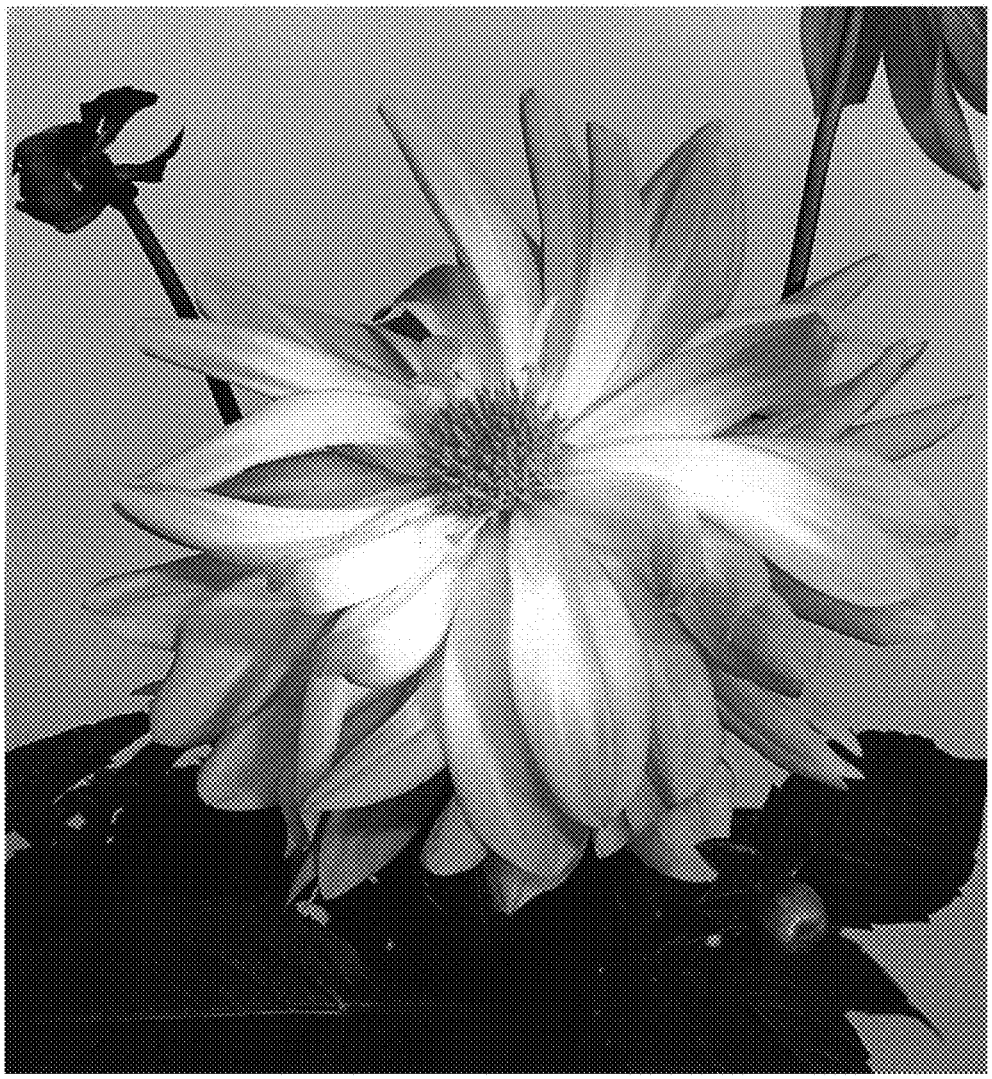

The photograph on the second sheet (FIG. 2) is a close-up view of a typical inflorescence of 'BKDAGIGP'.

DETAILED BOTANICAL DESCRIPTION

The aforementioned photographs and the following observations and measurements describe plants grown during the autumn and winter in 19-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were eleven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAGIGP'.

Parentage:

*Female, or seed, parent.*—*Dahlia hybrida* 'BKDAMAGRB', disclosed in U.S. Plant Pat. No. 30,691.

*Male, or pollen, parent.*—Proprietary selection of *Dahlia hybrida* identified as code number FET.S15.001.021, not patented.

Propagation:

*Type.*—By terminal cuttings.

*Time to initiate roots, summer.*—About 16 days at temperatures ranging from 18° C. to 21° C.

*Time to initiate roots, winter.*—About 19 days at temperatures about 21° C.

*Time to produce a rooted young plant, summer.*—About 21 days at temperatures ranging from 18° C. to 21° C.

*Time to produce a rooted young plant, winter.*—About 23 days at temperatures ranging from 19° C. to 21° C.

*Root description.*—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia*.

*Rooting habit.*—Moderately freely branching; medium density.

Plant description:

*Plant and growth habit.*—Relatively tall, upright to somewhat outwardly spreading and sturdy plant habit; overall plant shape, roughly globular; freely basal branching habit with about three primary branches each with about four secondary branches developing per plant; inflorescences held above the foliar plane on strong peduncles; bushy and dense growth habit; pinching is not required but will improve branching habit; vigorous growth habit and moderate growth rate.

*Plant height, soil level to top of foliar plane.*—About 29.3 cm.

*Plant height, soil level to top of floral plane.*—About 45.8 cm.

*Plant diameter or spread.*—About 44.1 cm.

*Lateral branches.*—Length: About 15.9 cm. Diameter: About 8 mm. Internode length: About 3.5 cm. Aspect: Primary branches are about 20° from vertical; secondary branches are about 25° from primary branch axis. Strength: Moderately strong to strong. Texture and luster: Sparsely pubescent; moderately glossy. Color, developing: Close to 146A. Color, developed: Close to 146A slightly tinged with close to 183B; at the internodes, close to 146A strongly tinged with close to 183B.

Leaf & leaflet description:

*Arrangement.*—Leaves opposite and compound with typically five leaflets and occasionally with three, seven or eleven leaflets.

*Length, leaves.*—About 22.1 cm.

*Width, leaves.*—About 19.4 cm.

*Length, terminal leaflets.*—About 11.8 cm.

*Width, terminal leaflets.*—About 6.9 cm.

*Length, lateral leaflets.*—About 10.5 cm.

*Width, lateral leaflets.*—About 5.2 cm.

*Shape, leaves.*—Broadly ovate in outline.

*Shape, leaflets.*—Ovate to elliptic.

*Apex, leaflets.*—Apiculate.

*Base, leaflets.*—Short to long attenuate.

*Margin, leaflets.*—Coarsely serrate to dentate.

*Venation pattern, leaflets.*—Pinnate.

*Texture and luster, upper surface, leaflets.*—Mostly smooth, glabrous with venation, moderately pubescent; slightly rugose; moderately glossy.

*Texture and luster, lower surface, leaflets.*—Mostly smooth, glabrous with venation, moderately pubescent; slightly rugose; slightly glossy.

*Color.*—Developing leaflets, upper surface: Slightly darker than 137A. Developing leaflets, lower surface: Close to 147B. Fully expanded leaflets, upper surface: Darker than 139A; venation, close to 146B. Fully expanded leaflets, lower surface: Close to between 147B and 191A; venation, close to 146B.

*Petioles.*—Length: About 5.2 cm. Diameter: About 3.5 mm by 4 mm. Strength: Moderately strong. Texture and luster, upper and lower surfaces: Moderately pubescent; glossy. Color, upper and lower surfaces: Close to 146B.

Inflorescence description:

*Appearance and arrangement*.—Large semi-double type inflorescences with ray and disc florets forming acropetally on a receptacle; inflorescences positioned above and beyond the foliar plane on strong peduncles; inflorescences face mostly upright to slightly outwardly; freely flowering habit with about 15 developing and fully developed inflorescences per plant at one time.

*Fragrance*.—None detected.

*Flowering response and flowering period*.—Early flowering habit, plants begin flowering about 68 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 3.8 cm. Diameter: About 3.9 cm. Shape: Broadly ovate; involucral bracts moderately reflexed. Texture and luster: Smooth, glabrous; glossy. Color: Close to 145B; proximally, close to 143A to 143B; distally, close to 70A to 70B; involucral bracts, close to NN137A.

*Inflorescence size*.—Diameter: Large, about 16 cm. Depth (height): About 9.4 cm. Disc diameter: About 2.9 cm.

*Receptacles*.—Height: About 5 mm. Diameter: About 1 cm. Shape: Lunate. Color: Close to between 150C and 150D.

*Ray florets*.—Quantity per inflorescence and arrangement: About 50 arranged in about four whorls. Length: About 7.5 cm. Width: About 2.8 cm. Shape: Narrowly obovate to oblanceolate; moderately to strongly carinate. Apex: Broad and bluntly acute. Base: Cuneate. Margin: Entire. Aspect: Mostly horizontal and somewhat curled upward. Texture and luster, upper surface: Smooth, glabrous; moderately velvety; matte. Texture and luster, lower surface: Smooth, glabrous; slightly velvety; mostly matte with venation, glossy. Color: When opening, upper surface: Distally, close to 72C and proximally, close to between 150D and 155C. When opening, lower surface: Distally, close to 72D and proximally, close to between 155C and 157D. Fully opened, upper surface: Distally, close to between 72D and 73A; proximally, close to NN155D and at the base, close to 1D; venation, close to NN155D; distal color becoming closer to 75A to 75B with subsequent development. Fully opened, lower surface: Distally, close to 73B; and proximally, close to NN155C and at the base, close to 157D; venation, close to N155B; color does not change with subsequent development.

*Disc florets*.—Quantity per inflorescence and arrangement: About 80 massed at the center of the inflorescence in about five spiral whorls. Length: About 1.9 cm. Diameter: About 9 mm. Shape: Tubular, elongated; lower 87.5% fused and upper 12.5% free; apices, acute and reflexed. Texture and luster, inner and outer surfaces: Smooth, glabrous; glossy. Color, when opening, inner and outer surfaces: Apex: Close to 21B. Mid-section: Close to 17A. Base: Close to 154B. Color, fully opened, inner and outer surfaces: Apex and mid-section: Close to 15A to 15B. Base: Close to 154B.

*Phyllaries*.—Quantity per inflorescence and arrangement: About five to seven arranged in a single whorl. Length: About 2.9 cm. Width: About 1.1 cm. Shape: Oblanceolate; proximally, strongly carinate. Apex: Acute. Base: Cuneate. Margin: Entire. Texture and luster, upper and lower surfaces: Smooth, glabrous; glossy. Color, upper surface: Close to NN137A. Color, lower surface: Close to NN137C; venation, close to 139A.

*Peduncles*.—Length, terminal peduncle: About 15.7 cm. Diameter, terminal peduncle: About 5 mm. Strength: Strong. Aspect: Mostly upright. Texture and luster: Smooth, glabrous; moderately glossy. Color: Close to N199A; proximally, close to N199B.

*Reproductive organs*.—Androecium, present on disc florets only: Quantity per floret: About five. Filament length: About 5 mm. Filament color: Close to 157D. Anther size: About 5 mm by 0.5 mm. Anther shape: Narrowly oblong. Anther color: Close to 13A and 13B. Pollen amount: Abundant. Pollen color: Close to 24A. Gynoecium, present on disc florets only: Quantity per floret: One. Pistil length: About 1.3 cm. Style length: About 8 mm. Style color: Close to 150D. Stigma diameter: About 9 mm. Stigma shape: Cleft. Stigma color: Close to 17A. Ovary color: Close to 145D. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Garden performance: Plants of the new *Dahlia* have been observed to have good garden performance, to tolerate high temperatures of about 35° C. and to be suitable for USDA Hardiness Zones 9 to 11.

It is claimed:

1. A new and distinct *Dahlia* plant named 'BKDAGIGP' as illustrated and described.

* * * * *